(12) United States Patent
Luxembourg (10) Patent No.: US 10,877,262 B1
(45) Date of Patent: Dec. 29, 2020

(54) MAGNIFICATION GLASSES WITH MULTIPLE CAMERAS

(71) Applicant: Itzhak Luxembourg, Beit Elazari (IL)

(72) Inventor: Itzhak Luxembourg, Beit Elazari (IL)

(*) Notice: Subject to any disclaimer, the term of this patent is extended or adjusted under 35 U.S.C. 154(b) by 0 days.

(21) Appl. No.: 16/625,780

(22) PCT Filed: Jun. 21, 2018

(86) PCT No.: PCT/IL2018/050691
§ 371 (c)(1),
(2) Date: Dec. 23, 2019

(87) PCT Pub. No.: WO2018/235088
PCT Pub. Date: Dec. 27, 2018

Related U.S. Application Data (60) Provisional application No. 62/522,692, filed on Jun. 21, 2017.

(51) Int. Cl.
| | |
|---|---|
| *G02B 26/00* | (2006.01) |
| *G02B 25/00* | (2006.01) |
| *G02B 27/01* | (2006.01) |
| *A61B 1/24* | (2006.01) |
| *A61B 6/00* | (2006.01) |

(52) U.S. Cl.
CPC .............. *G02B 25/004* (2013.01); *A61B 1/24* (2013.01); *A61B 6/462* (2013.01); *A61B 6/466* (2013.01); *G02B 27/0172* (2013.01); *G02B 2027/0138* (2013.01); *G02B 2027/0178* (2013.01)

(58) Field of Classification Search
CPC .. G02B 27/0172; G02B 25/004; G02B 25/00; G02B 2027/0138; G02B 2027/0178; G02C 7/08; G02C 9/00; A61B 6/462; A61B 6/466
USPC ......................................................... 351/158
See application file for complete search history.

(56) References Cited

U.S. PATENT DOCUMENTS

| | | | |
|---|---|---|---|
| 4,195,918 | A | 4/1980 | Freche et al. |
| 6,307,526 | B1* | 10/2001 | Mann .................... H04N 5/2254 345/8 |
| 10,459,254 | B2* | 10/2019 | Antaki ................. H04N 5/2258 |
| 2015/0293345 | A1 | 10/2015 | Laxhuber et al. |
| 2016/0334644 | A1* | 11/2016 | Garofolo .................. G02C 7/14 |
| 2016/0358327 | A1 | 12/2016 | Lemchen |
| 2017/0068119 | A1* | 3/2017 | Antaki ................. H04N 5/2258 |
| 2020/0004052 | A1* | 1/2020 | Antaki ............... G02B 27/0093 |

FOREIGN PATENT DOCUMENTS

| | | |
|---|---|---|
| IL | 244255 A | 4/2017 |
| WO | 2008/015002 A1 | 2/2008 |

* cited by examiner

*Primary Examiner* — William R Alexander
(74) *Attorney, Agent, or Firm* — Alphapatent Associates, Ltd; Daniel J. Swirsky (57) ABSTRACT

Magnification glasses and methods of use, the glasses including a first camera array for capturing a magnified image in the field of view of the glasses, the first camera array including a first camera and a second camera, where the first camera and the second camera provide different levels of magnification, where the first camera and the second camera have the same working distance of between 150 mm to 400 mm, and where the first camera and the second camera are fixed focus cameras.

20 Claims, 9 Drawing Sheets

MAGNIFICATION GLASSES WITH MULTIPLE CAMERAS

FIELD OF THE INVENTION

The present invention relates generally to magnification glasses and more specifically to magnification glasses that comprise multiple cameras each with the same working distance but providing different magnification.

BACKGROUND OF THE INVENTION

For many medical and industrial applications it is useful for the practitioner to have a magnified view of the work surface or patient. For example, dentists often need to magnify the area being worked on in the patient's mouth. Other practitioners needing close range magnified views include dermatologists, surgeons, gemologists such as for viewing gems, or agronomists such as for inspecting leaves and other plant parts. In the past this was most often achieved by wearing a headset or pair of glasses with optical loupes attached. In use, the loupes are generally swiveled into position in front of the practitioner's eyes when magnification is required and then swiveled away when not required. Achieving different levels of magnification usually requires swapping the loupe lenses. Optical loupes are relatively heavy due to their glass lenses and stick out once in position, occupying between 3-10 cm of space in front of the practitioner's eyes. Further—they are often fixed inside the glasses—permanently obstructing the view and requiring switching of glasses for different magnifications.

An alternative to the optical loupe is use of a digital loupe comprising a digital camera that feeds an image to a small screen. As with the optical loupe solution the camera/screen combination can be mounted onto a headband or mounted as part of the glass in front of the practitioner's eyes when magnification is required. The image from the digital camera can then be digitally zoomed for greater magnification. The disadvantage of digital zoom is that the quality of the image suffers as the zoom is increased due to the reduced number of pixels in use, and therefore the range of magnification is limited. The use of optical magnification combined with a digital camera is possible but requires the use of auto-focus digital cameras which are more expensive and also heavier than the non-auto-focus equivalents.

The background art therefore does not teach or suggest a system for close range magnification glasses using cost-effective digital cameras that can provide an extended range of magnification. It would also be desirable to be able to capture and transmit the view as seen through the magnification device.

SUMMARY OF THE INVENTION

The presently claimed invention provides wearable glasses featuring variable magnification of close range subjects by using camera array comprising a plurality of cost-effective fixed focus, fixed distance, fixed magnification digital cameras each providing different magnification while maintaining the same working distance. The image captured by the camera array is displayed to the user using viewing assemblies that are one of: screens placed in front of the glasses; or image projection onto the glasses lenses, or a headset comprising viewing screens. The image displayed may be any of: the magnified view captured by the camera array; or virtual reality, or augmented reality; or any of these overlaid with relevant textual or image data. Optionally, infrared images or images lit with ultraviolet light are provided.

The use of multiple fixed focus cameras each providing output images of different magnification for a fixed working distance lowers the cost of implementation, results in a magnification device with a more compact and lighter form factor, and increases the magnification range for digital camera based magnification glasses. The close range fixed working distance is preferably between 10-40 cm.

Each of the fixed focus cameras in the array has a lens providing different maximum magnification allowing for fast switching between different levels of magnification. In an exemplary and preferable embodiment a first camera lens provides up to 6× magnification and a second camera lens provides up to 10× magnification. Alternatively a first camera lens provides up to 5× magnification and a second camera lens provides up to 10× magnification. Alternatively any combination of cameras is provided for the magnification and working distance required by the particular application. Optionally more than two cameras may be provided per array.

The images captured by each camera in the array are provided to a processing unit that outputs a selected image from one of the cameras depending on the magnification required. Digital magnification of the output image is preferably provided from the camera with the lowest magnification lens up till the camera with the highest magnification lens with a seamless switch of the output image between the image captured from the first camera and the image captured from the second camera.

Preferably the captured image is displayed on one or both of the left and right viewing assemblies. Alternatively the camera array may be duplicated with each array feeding a respective left or right viewing assembly to therefore provide magnified stereoscopic vision. The control of the magnification provided is via any suitable control device including but not limited to a joystick, foot pedal, speech control, switch mounted on the glasses or attached to them or similar. The image captured by the cameras can preferably be saved such as to non-volatile storage or transmitted for display on a local or remote display. The image displayed can preferably be overlaid with relevant textual or image data. The displays can preferably be divided into a bifocal arrangement for display of different views or overlay data on different parts of each display.

According to at least some embodiments of the present invention, there are provided magnification glasses comprising: a first camera array for capturing a magnified image in the field of view of the glasses comprising at least a first camera and a second camera wherein each of the first camera and the second camera provide different levels of magnification, wherein the first camera and the second camera have the same working distance. Preferably the working distance is fixed between 150 mm to 400 mm. Preferably each of the first and second cameras provides a different magnification of between 2× and 10×. Preferably the working distance is fixed in a subrange between 150 mm to 400 mm. Preferably the working distance is fixed in a range between 150 mm to 400 mm.

Preferably the glasses further comprise a first viewer assembly and a processor, wherein the processor receives a first magnified image captured by the first camera and a second magnified image captured by the second camera and transmits either one of the first image or the second image for display on the first viewer assembly, wherein the processor is a computing device. Preferably the processor digitally zooms either one of the first magnified image or the second magnified image before transmission to the first viewer assembly.

Preferably the first viewer assembly comprises at least one of: a display screen positioned in front of the glasses frame; a display screen mounted in the glasses frame; or a projector for projecting on a lens in the frame. Optionally one or more of the cameras comprises an infrared camera. Preferably the processor provides for display on the viewer assembly at least one of: the magnified view captured by the camera assembly; a virtual reality view; an augmented reality view; a data view; or an infrared view.

Preferably the glasses further comprise a second camera array and a second viewer assembly positioned on the same side of the glasses, wherein the first camera array and a first viewer assembly are positioned on the opposite side of the glasses wherein the first and second camera arrays are spaced horizontally apart so as to capture stereoscopic vision, wherein the the processor transmits the image from the first camera array to the first viewer assembly and wherein the processor transmits the image from the second camera array to the second viewer assembly.

Optionally the camera arrays are mounted on the glasses. Alternatively the camera arrays are mounted on a headband. Preferably each camera comprises a lens and an image sensor. Preferably the processor is housed inside the frames. Optionally the processor is housed in an external enclosure. Preferably the glasses further comprise a controller selected from the group consisting of: a joystick, a foot pedal, speech control, and a switch. Preferably the glasses further comprise an illumination source. Optionally the illumination source comprises an ultraviolet light.

According to further embodiments of the present invention, there are provided electro-optical magnifying glasses comprising: a wearable display; and a first camera array for capturing a magnified image in the field of view of the glasses comprising at least a first camera and a second camera wherein each of the first camera and the second camera provide different levels of magnification, wherein the first camera and the second camera have the same working distance. Preferably the working distance is fixed between 150 mm to 400 mm. Preferably each of the first and second cameras provides a different magnification of between 2× and 10×.

Preferably the glasses further comprise a processor, wherein the processor receives a first magnified image captured by the first camera and a second magnified image captured by the second camera and transmits either one of the first image or the second image for display on the display, wherein the processor is a computing device. Preferably the processor digitally zooms either one of the first magnified image or the second magnified image before transmission to the first viewer assembly. Optionally one or more of the cameras comprises an infrared camera.

Preferably the processor provides for display on the display of at least one of: the magnified view captured by the camera assembly; a virtual reality view; an augmented reality view; a data view; or an infrared view.

According to further embodiments of the present invention, there are provided magnification glasses comprising: wearable glasses frames with lenses; a first camera array comprising at least two fixed focus cameras capturing a magnified view of the field of view of the glasses; and a viewer assembly comprising at least one of: a display screen in front of at least one of the lenses for displaying at least the magnified view from one of the cameras; or a projector for projecting at least the magnified view from one of the cameras on at least one of the lenses. Preferably the glasses further comprise a second camera array wherein each of the first and second arrays are spaced horizontally apart so as to capture stereoscopic vision. Optionally the camera arrays are mounted on the glasses. Optionally the camera arrays are mounted on a headband.

Preferably each camera comprises a lens and an image sensor and preferably the lens provides a magnification of between 2× and 10×. Preferably each camera comprises a graphics card. Preferably each camera has a working distance of 150 mm to 400 mm. Preferably the glasses further comprise a processor for receiving the image captured by the cameras and transmitting the image to the display screen or the projector, wherein the processor is a computing device. Optionally the processor is housed inside the frames. Optionally the processor is housed in an external enclosure.

Preferably the viewer assembly can be swiveled away from the frames. Preferably the viewer assembly displays at least one of: a magnified view captured by the cameras; a virtual reality view; an augmented reality view; a data view, or a combination of these. Preferably the glasses further comprise a controller selected from the group consisting of: a joystick, a foot pedal, speech control, and a switch.

According to further embodiments of the present invention, there are provided magnification glasses comprising: wearable glasses frames; at least two fixed focus camera capturing a magnified view of the field of view of the glasses; and a display screen in front of the glasses for displaying the magnified view from one of the cameras.

As used herein the term "image" is used to described the digital capture from the cameras but it should be appreciated that in practice a stream of images or video is captured and the term image as used herein covers all of these capture types. The term "magnification glasses" may also refer to "loupe glasses".

The terms "camera array" or "camera assembly" or "camera set" as used herein refer to a set of cameras each with different magnification or other capabilities.

The term "close range" as used herein refers to a distance of 10-40 cm. The term "working distance" as used herein is the distance wherein the image captured by the cameras is in focus.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computing device", a "computer", or "mobile device", it should be noted that optionally any device featuring a data processor and the ability to execute one or more instructions may be described as a computer, including but not limited to any type of personal computer (PC), single board computer (SBC), field-programmable gate array (FPGA), a server, a distributed server, a virtual server, a cloud computing platform, a cellular telephone, an IP telephone, a smartphone, or a PDA (personal digital assistant). Any two or more of such devices in communication with each other may optionally comprise a "network" or a "computer network".

BRIEF DESCRIPTION OF THE DRAWINGS

The invention will now be described in connection with certain preferred embodiments with reference to the following illustrative figures so that it may be more fully understood. With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

In all the figures similar reference numerals identify similar parts.

DETAILED DESCRIPTION OF PREFERRED EMBODIMENTS

Figure 1A:
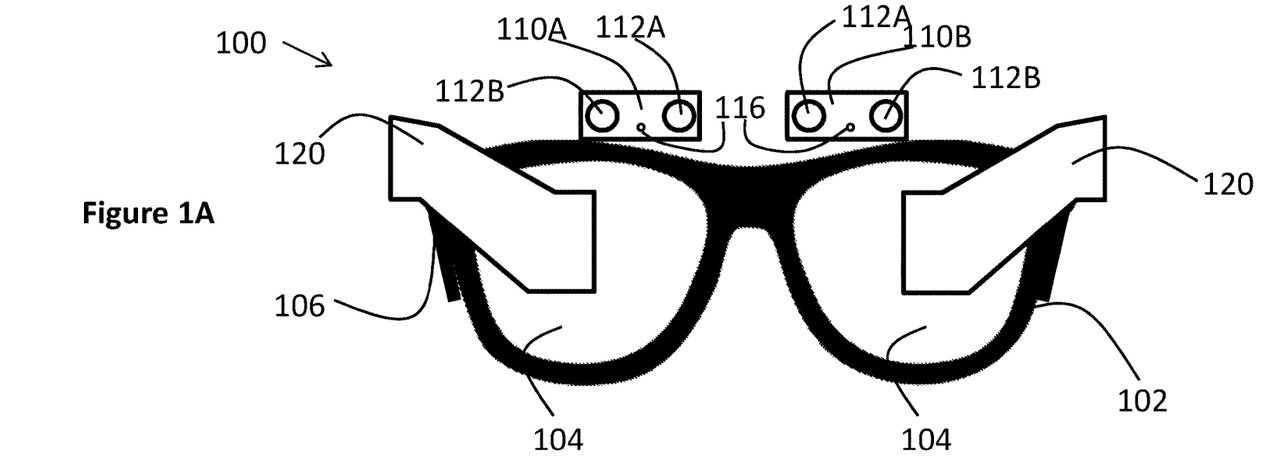
FIGS. 1A-1E, are illustrations of magnification glasses according to at least some embodiments of the present invention.
Figure 1B:
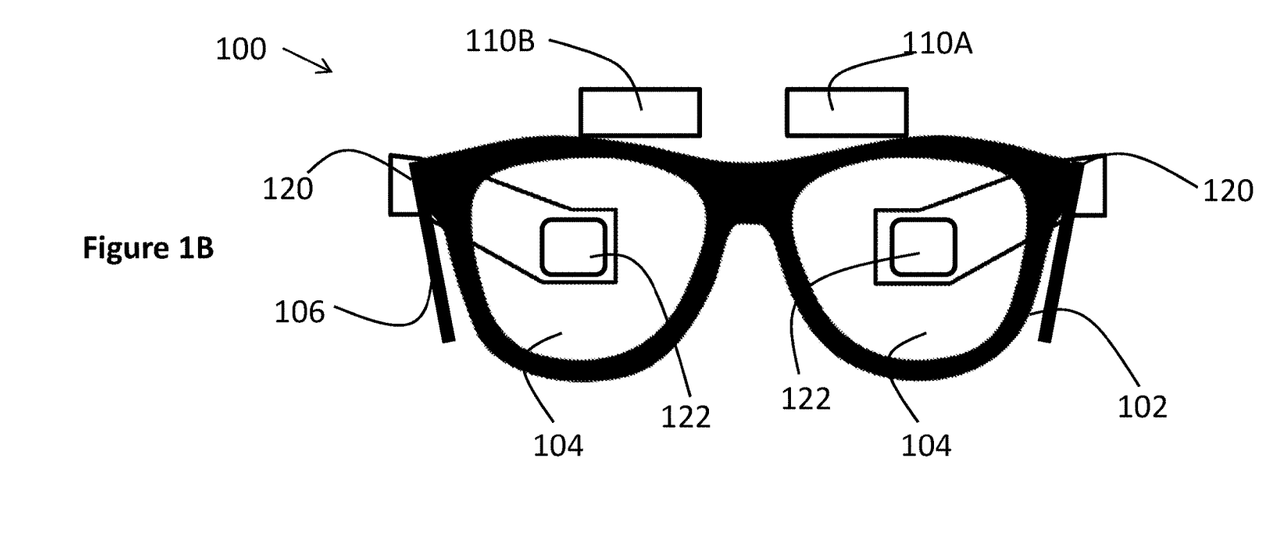
Figure 1C:
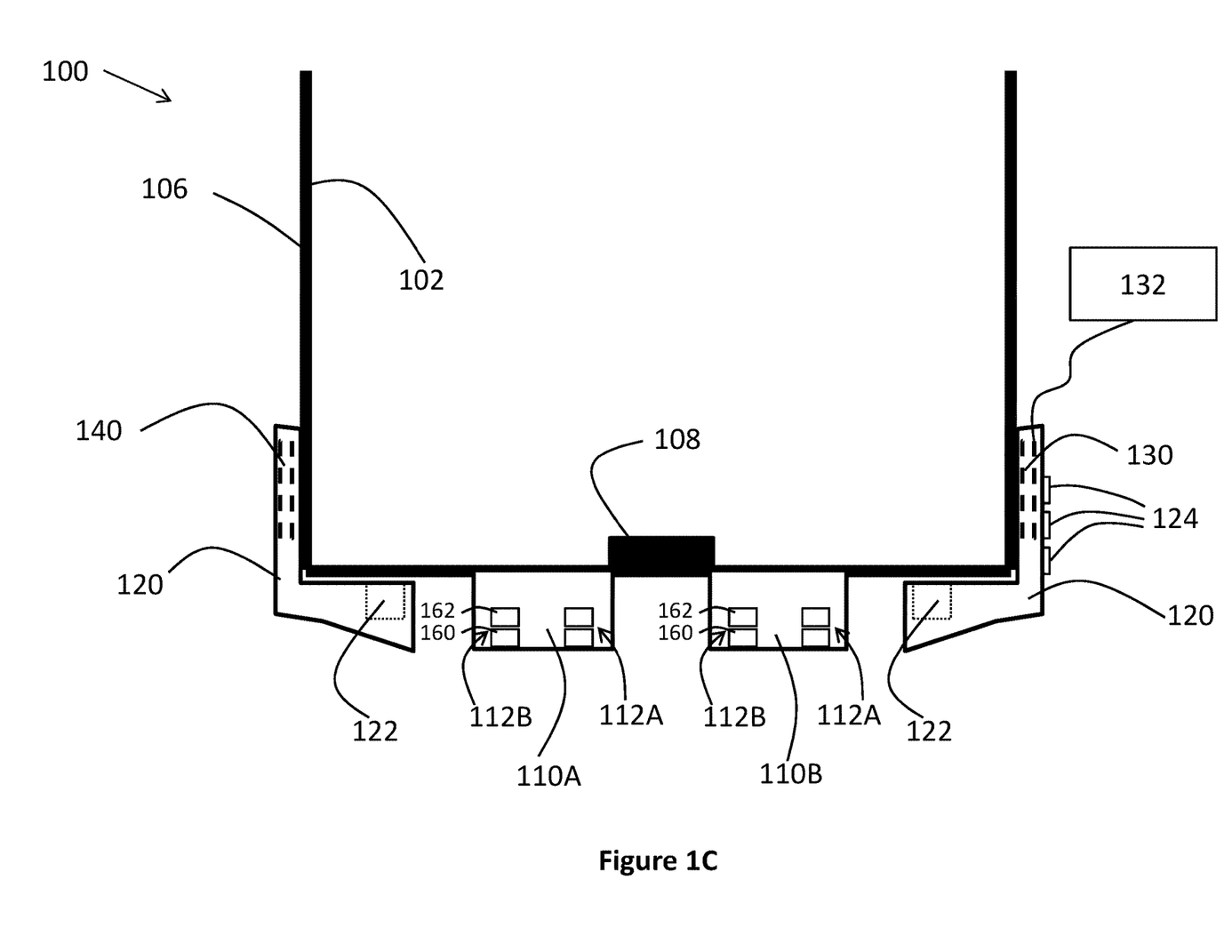
Figure 1D:
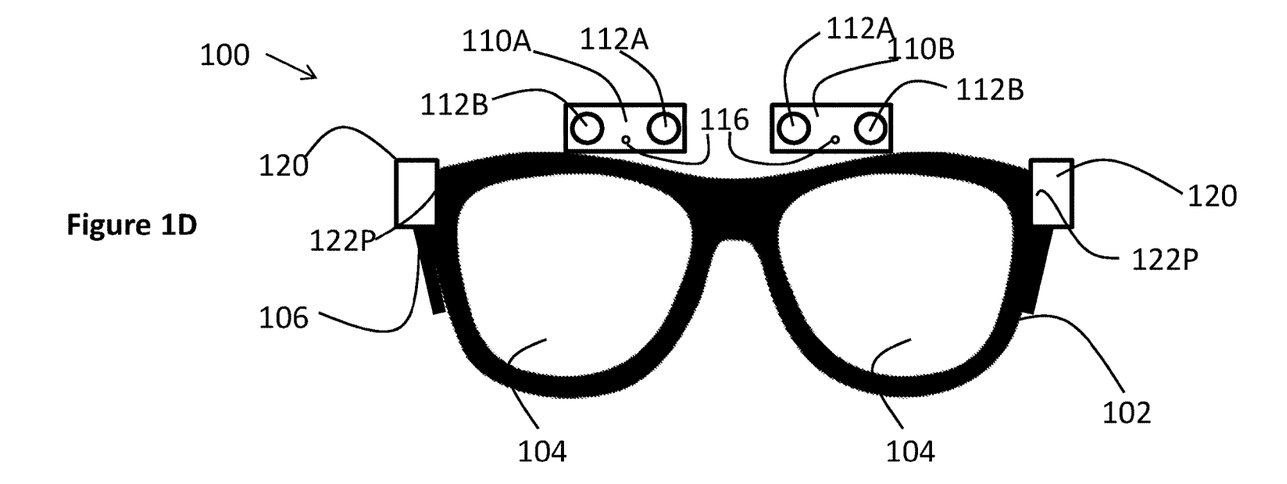
Figure 1E:
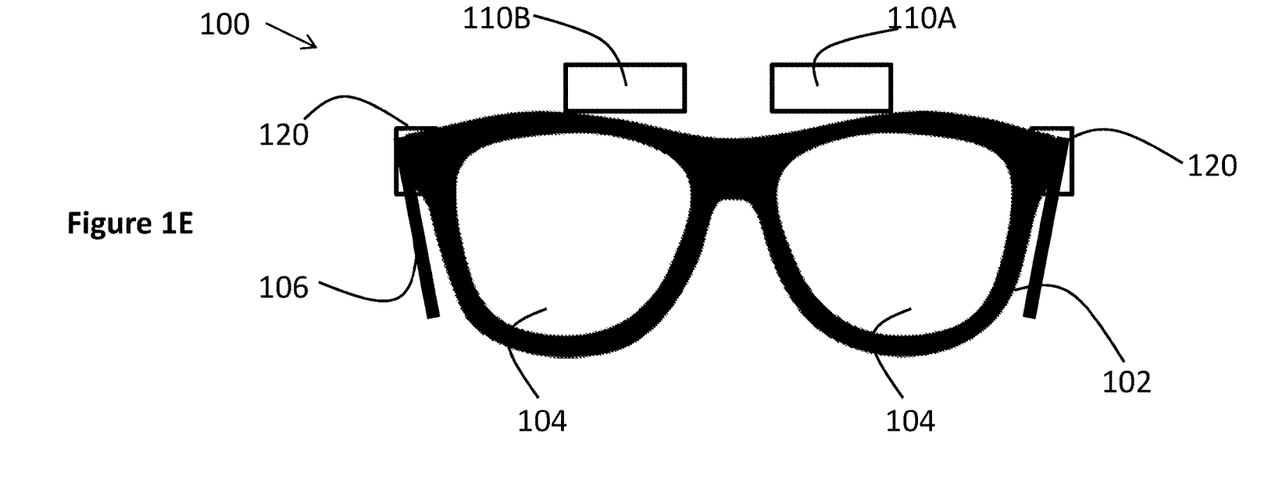

The present invention will be more fully understood from the following detailed description of the preferred embodiments thereof, taken together with the drawings. Reference is now made to FIGS. 1A-1E, which show magnification glasses according to at least some embodiments of the present invention. FIGS. 1A and 1D shown a front view of the magnification glasses 100, FIGS. 1B and 1E show a rear view of the magnification glasses 100, and FIG. 1C shows a top view of the magnification glasses 100.

As shown, glasses 100 comprise a glasses frame 102 as known in the art. Frame 102 is shaped as a frame of a standard pair of glasses as known in the art and is made from materials as known in the art such as plastic or any other suitable material. The design of frame 102 as shown in the figures should not be considered limiting. Glasses 100 comprise lenses 104. Lenses 104 are optically clear and manufactured from glass or plastic or other composite material as known in the art. Lenses 104 are optionally adapted to the optical needs of the specific wearer such as featuring prescription lenses. In some embodiments, lenses 104 are optionally coated with reflective materials to enable projection of an image thereon as will be described further below. Optionally lenses 104 are not provided such as when viewer 122 comprises a display screen 122S.

Frames comprise arms 106 wherein arms 106 fit over the ears of the wearer and nose bridge 108 for supporting glasses 100 on the nose of the wearer as known in the art.

A camera assembly 110 is mounted on top of frame 102. In the embodiment as shown, two camera assemblies 110A and 110B are provided, each providing information for the view provided to the left or right eye so as to enable stereoscopic vision where the camera assembly 110A on the right provides for the image of the right eye and the camera assembly 110B on the left provides for the image of the left eye. Each camera assembly 110 comprises at least two cameras 112 however the embodiment as shown should not be considered limiting and more than two cameras 112 may be provided.

In a preferred embodiment first camera 112A and second camera 112B each comprise a lens 160, and image sensor 162. Optionally any suitable combination of lens 160 and image sensor 162 are used and the specifications provided below should not be considered limiting. Cameras 112 are chosen with differing specifications resulting in a fixed working distance that suits the close range working environment. Camera specifications include but are not limited to apertures, sensor size, focal length, FOV (field of view), DOF (depth of field), and so forth. Camera 112 has a fixed working distance of between 100-400 mm. Different lens and camera combinations are preferably chosen to provide specific fixed close range working distances adapted to the specific application.

An exemplary lens of first camera 112A is a 25 mm FL f/8 lens such as the Blue Series M12 Video™ Imaging Lens with the following specifications:

Focal Length FL (mm): 25.0

Aperture (f/#): f/2.5

Working Distance (mm): 150-400

Maximum Camera Sensor Format: ½"

Distortion (%): 0.3 Diagonal, 0.14 Horizontal

Field of View: ½"

Sensor: 35-60 mm

Length (mm):30.0

Outer Diameter (mm):14.0

An exemplary lens of second camera 112B is a 10 mm FL f/8, such as the Blue Series M12 Video™ Imaging Lens with the following specifications:

Focal Length FL (mm):10.0

Aperture (f/#):f/8

Working Distance (mm):150-400

Maximum Camera Sensor Format:⅓"

Distortion (%):−1.5 Diagonal, −0.87 Horizontal

Field of View, ⅓"

Sensor:72-120 mm

Length (mm):17

Outer Diameter (mm):14.0

In each camera 112 the lens 160 is fitted to an image sensor 162. An exemplary image sensor 162 such as provided in each of cameras 112A and 112B is the CAM130_CUMI1820_MOD 13 MP camera such as provided by e-con Systems™ with the following specifications:

CMOS Image Sensor from Aptina™/ON Semiconductor®
1.25 μm pixel size with Aptina/ON Semiconductor A-PixHS™ BSI technology
1/2.3" optical form-factor
Dynamic Range: 65.8 dB
SNRMAX: 36.3 dB
Electronic Rolling Shutter
Responsivity: 0.62V/lux-sec As above, image sensor 162 is chosen along with lens 160 to provide a specific magnification and working distance and the exemplary image sensor described above should not be considered limiting.

As above, additional cameras 112 may be added to camera assembly 110 wherein each additional camera 112 provides a different level of magnification while maintaining the same working distance as other cameras 112 in camera assembly 110. Optionally, camera 112 comprises an infrared (IR) camera (not shown) capable of capturing IR images wherein processor 130 converts the captured IR images into images in the visible spectrum for display on viewer assemblies 120.

Camera assembly 110 optionally comprises an illumination source 116 which may be any of an LED, LED array, or fiber optic array or any other illumination source. Optionally illumination source 116 comprises an ultraviolet (UV) light.

Figure 2:
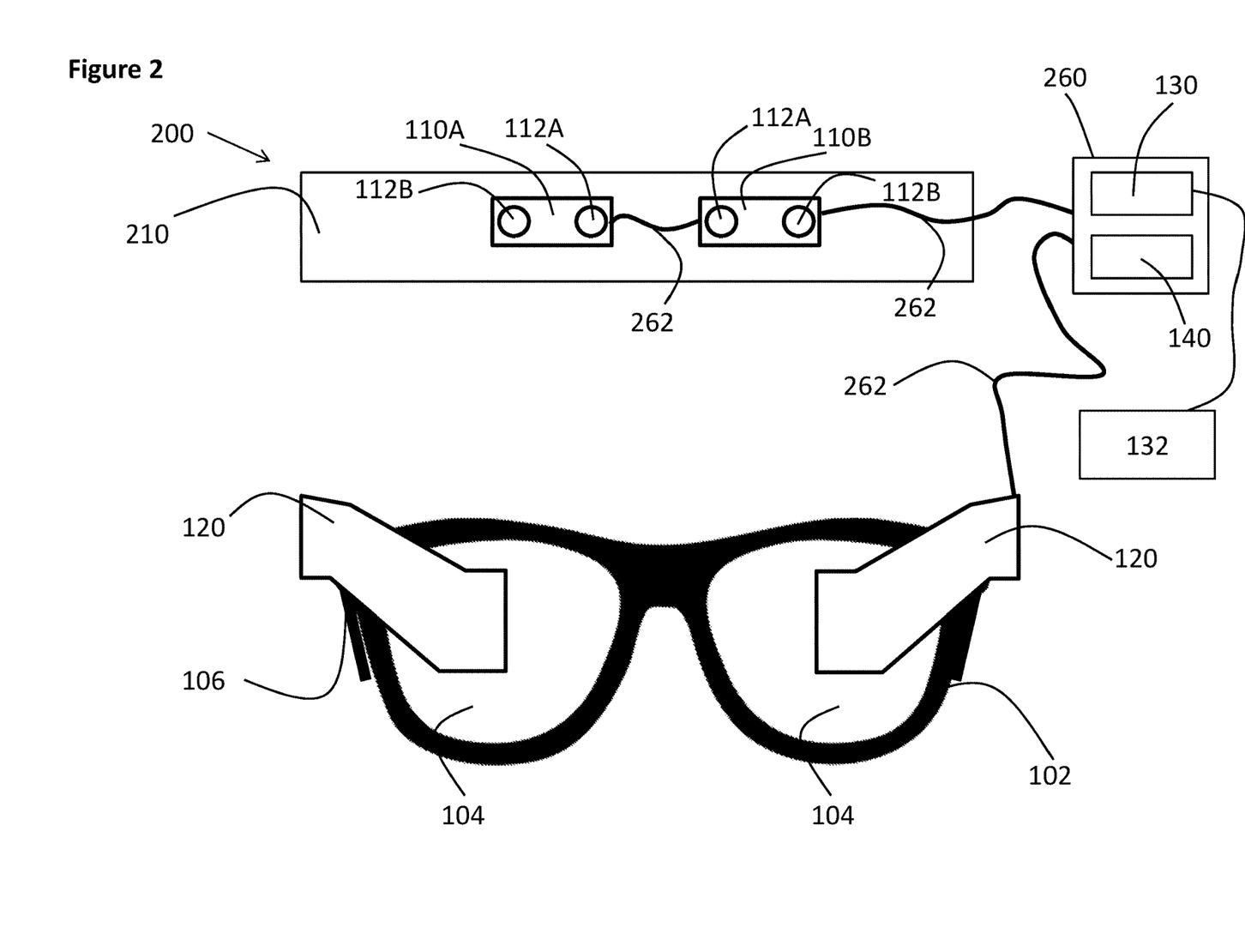
FIG. 2 is an illustration of magnification glasses according to at least some embodiments of the present invention.

Camera assembly 110 is connected to a processor 130 and a power source 140. As shown (FIG. 1C) processor 130 and power source 140 are embedded inside frame 102. Optionally processor 130 and power source 140 are provided in an external enclosure 260 (FIG. 2A). The electrical connections between camera assembly 110 and processor 130 and power source 140 are made using cables embedded inside frame 102. Where an external enclosure 260 is provided, the cables 262 are visible connecting the components of glasses 200. Although an external enclosure 260 is shown as part of the embodiment of FIG. 2A, it should be appreciated that alternative embodiments are possible such as the glasses 100 with an external enclosure or the glasses 200 with processor 130 and power source 140 embedded within frame 102. The image sensor 162 of each camera 112 communicates with processor 130 using any suitable protocol such as the non-liming example of the MIPI Camera Serial Interface.

Processor 130 is a computing device as defined herein. Processor 130 is preferably in wireless or wired communication with an external processor (not shown) or data source such as a server (not shown). A non-limiting example of processor 130 is a Qualcomm® Snapdragon™ 410/410E processor. A non-limiting example of an external processor is an Intel® Core i7-5557U. Non-limiting examples of power source 140 include a battery or wired mains connection with a voltage adaptor.

Optionally glasses 100 are connected to an external camera 132 by either wired or wireless connection. The image captured by external camera 132 is provided to processor 130 for transmitting to viewer assembly 120.

Viewer assembly 120 is mounted on the side of frame 102. Viewer assembly 120 comprises viewer 122 and associated electronics (not shown). Viewer assembly 120 is shown here as duplicated with one viewer assembly 120 per eye of the user. Optionally, only one viewer assembly 120 is provided. Optionally, viewer assembly 122 can be tilted away from lenses 104 so as not to obstruct the view of the practitioner when viewer assembly 120 is not needed. Viewer assembly 122 can optionally be tilted upwards or to the sides. The position of viewers 122 as shown is illustrative and should not be considered limiting.

As shown in FIGS. 1A-1C, viewer 122 comprises a display screen 122S that is viewed by the user through lenses 104. A non-limiting example of such a screen is the Vufine+™.

In an alternative embodiment as shown in FIGS. 1D-1E, viewer 122 comprises a projector 122P for projecting an image onto lenses 104. A non-limiting example of such a projector 122P is the Lumus™ OE33 with the following specifications:
Resolution: 1280×720
FOV: Diagonal 40°
Configuration: Side-mounted
Orientation: Landscape
Transparency: True see-through Controller buttons 124 are integrated into viewer assembly for control of the functioning of glasses 100. Alternatively controller buttons are provided on a separate controller (not shown) that is connected wirelessly or wired to processor 130. Non-limiting examples of controller buttons 124 include a joystick, foot pedal, speech control, switch mounted on glasses 100 or attached to glasses 100 or similar Control of glasses 100 by controller buttons 124 includes but is not limited to powering on and off, selecting the view shown on viewer 122, activating illumination source 116, activating UV light (not shown), and so forth.

Reference is now made to FIG. 2 which is an illustration of magnification glasses according to at least some embodiments of the present invention. The components of glasses 200 as shown in FIG. 2 are the same as those of FIGS. 1A-1C, however, in the embodiment of FIG. 2, camera assembly 110 is mounted on a headband 210. Cables 262 interconnect camera assemblies 110, viewer assemblies 120, processor 130 and power source 140 where processor 130 and power source 140 are provided inside enclosure 260. Where possible, cables (not shown) are embedded inside frames 102.

Reference is now made to FIGS. 3A-3F which are illustrations of the use of magnification glasses according to at least some embodiments of the present invention. The usage is illustrated with the embodiment of FIGS. 1A-1C and also 1D-1E as indicated below, however glasses 200 of FIG. 2 are also used in the same way as illustrated in FIGS. 3A-3F and as described herein and therefore the description should be considered to include these. The views of FIGS. 3A-3F are rear views showing the user view through glasses 100 or 200. The illustrated non-limiting application is use of the glasses such as by a dentist or oral hygienist. Any other usage is possible and the use of the glasses of the present invention is not limited to dentistry.

Figure 3A:
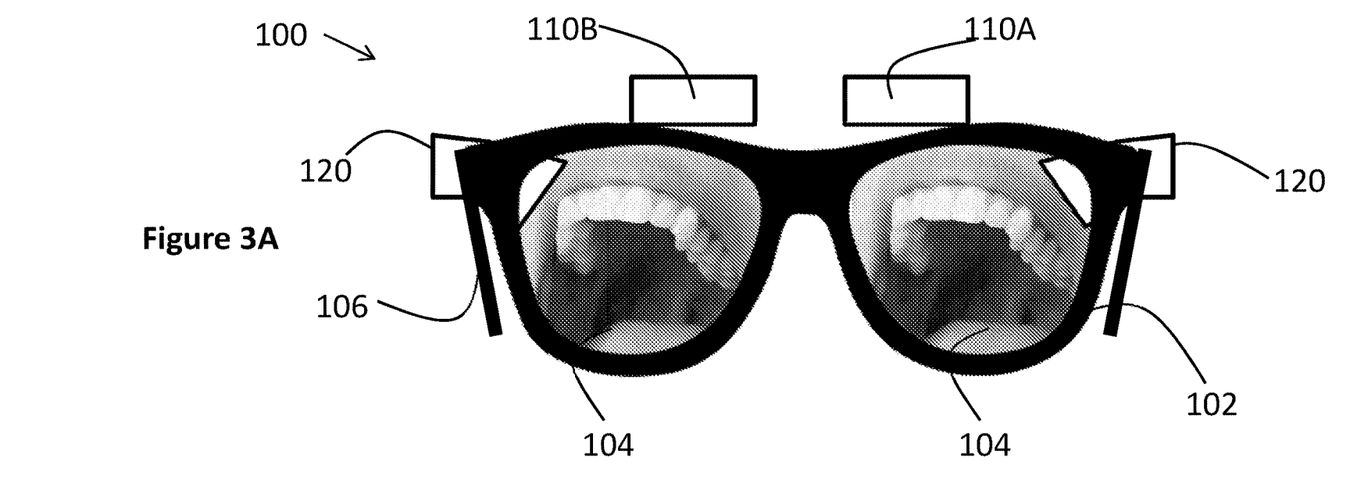
FIGS. 3A-3F are illustrations of the use of magnification glasses according to at least some embodiments of the present invention.

As shown in FIG. 3A, a user sees an unaided view of a patient through the lenses 104 of glasses 100. In the embodiment of FIGS. 1A-1C, viewer assemblies 120 are swiveled sideways so as not to obstruct the view of the user.

Figure 3B:
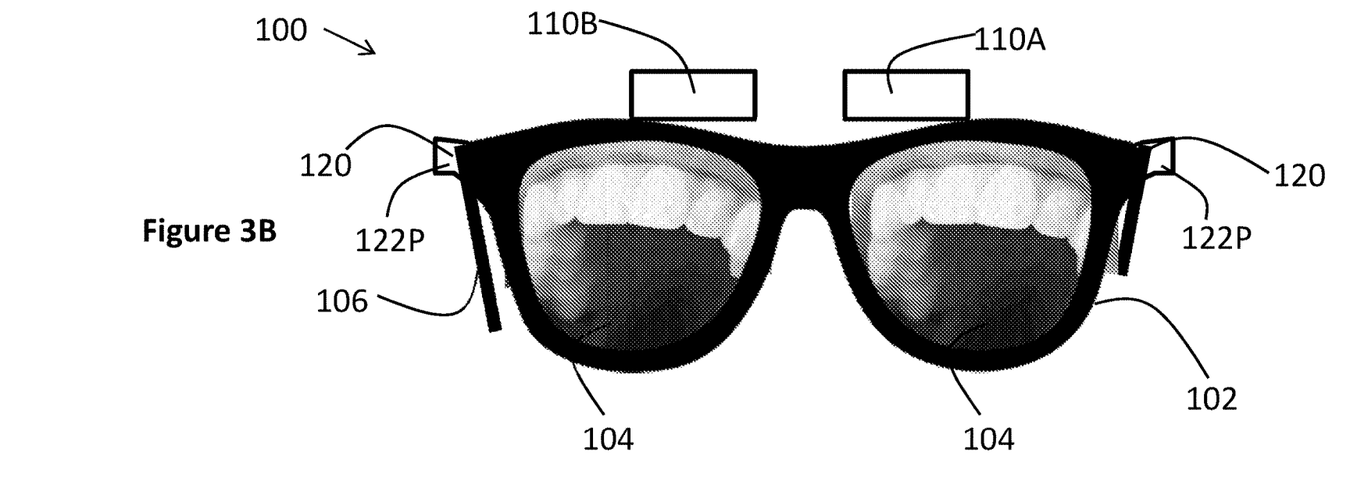

In FIG. 3B, based on the embodiment of FIGS. 1D-1E, the user chooses to view a magnified view of the patient and selects a first level of magnification using buttons 124. This first level of magnification is provided by first camera 112A. The video from first camera 112A is communicated to processor 130 and processor 130 connects the video to viewer assemblies 120. When there are left and right first cameras 112A, their respective video streams are connected to left and right viewer assemblies 120 respectively and viewer assemblies 120 use left and right projectors 122P to project the magnified image onto lenses 104 as shown.

Figure 3C:
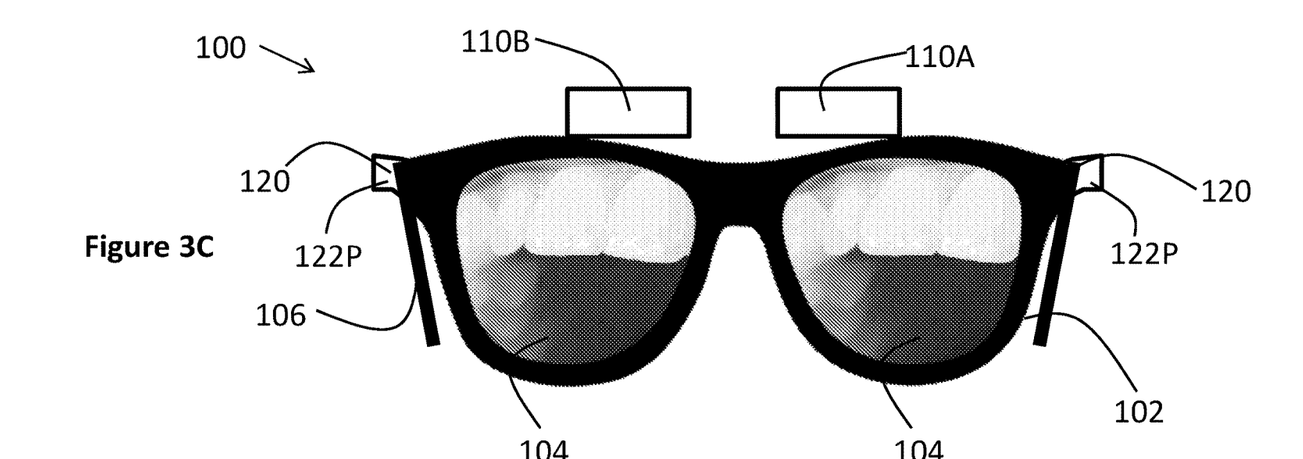

FIG. 3C depicts the view after the user has again selected to increase the magnification by pressing the appropriate button 124. In this case the image from the first camera 112A is digitally zoomed and then at a predefined crossover point the feed to viewer assembly 120 is switched to the second level of magnification provided by second camera 112B. The video from second camera 112B is communicated to processor 130 and processor 130 connects the video to viewer assemblies 120 where viewer assemblies 120 use projectors 122P to project the magnified image onto lenses 104 as shown. When there are left and right second cameras 112B, their respective video streams are connected to left and right viewer assemblies 120 respectively. As above, there may optionally be more cameras 112 each with a set magnification level which is selected by the processor depending on the control of the user such that as a user activates buttons 124 for increased magnification the view shown by viewer assembly 120 is magnified as shown in FIG. 3G. Further, as above, there may be cameras 112 with different capabilities such as IR or external cameras, and the images captured from these may be selected using controller buttons 124 for display on viewer assemblies 120.

Figure 3D:
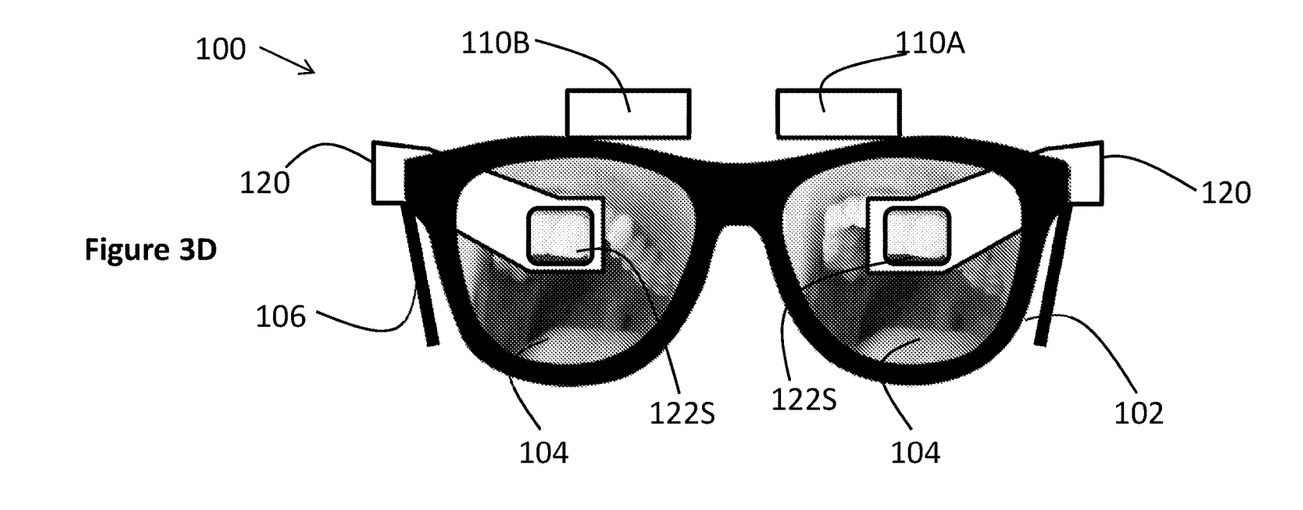
Figure 3E:
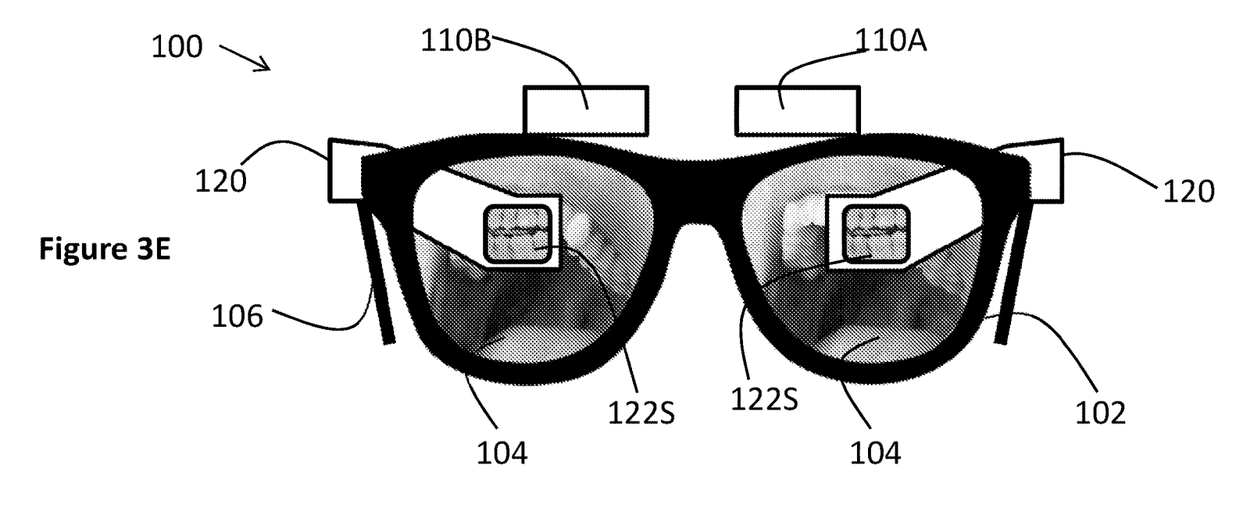

Depending on the type of viewer 122 used, the method of displaying the magnified view will vary as follows:

When viewer 122 is a display screen 122S such as shown in FIG. 3D, the magnified or other view is shown on viewer 122S;

When viewer 122 is a projector 122P such as shown in FIGS. 3B, 3C, 3E and 3F, the magnified or other view is projected on the front of lenses 104.

Figure 3F:
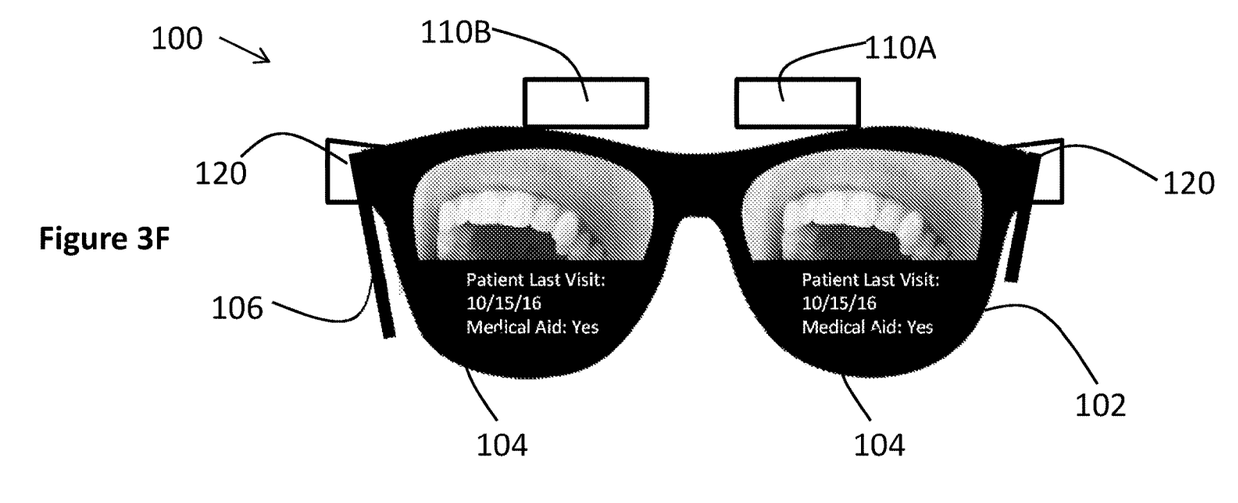

The type of video or image shown on the screen 122S or projection 122P may be any one of the following:

Magnification: where the view is the magnified video or image captured by camera assembly 110;

Virtual reality (VR): where the projected VR view is constructed by processor 130 or alternatively by a connected external processor (not shown); Augmented reality (AR): Where the view captured by camera assembly 110 is augmented with data or other indications where the AR view is constructed by processor 130 or alternatively by a connected external processor (not shown);

Data view: where data related to the particular application is displayed to the user. In a non-limiting example for a dentistry application the viewer 122S could display an x-ray of the mouth of the patient such as in FIG. 3E. In a further non-limiting example a bifocal view as in FIG. 3F shows patient data on a bottom portion of the lens with the magnified or unmagnified view visible in the upper portion of the lens. Alternatively the split view may divide the lens in left and right portions, or multiple portions other than those shown. Preferably the same view is shown on each lens but optionally the view is different. The data for this data view is provided by an external data source that is connected to glasses 100 or 200;

Infrared view: where the view is the IR video or image captured by camera assembly 110 when camera assembly 110 comprises at least one IR camera;

External camera view: where the view is the view captured by an external camera 132 connected to glasses 100 or 200.

Figure 4A:
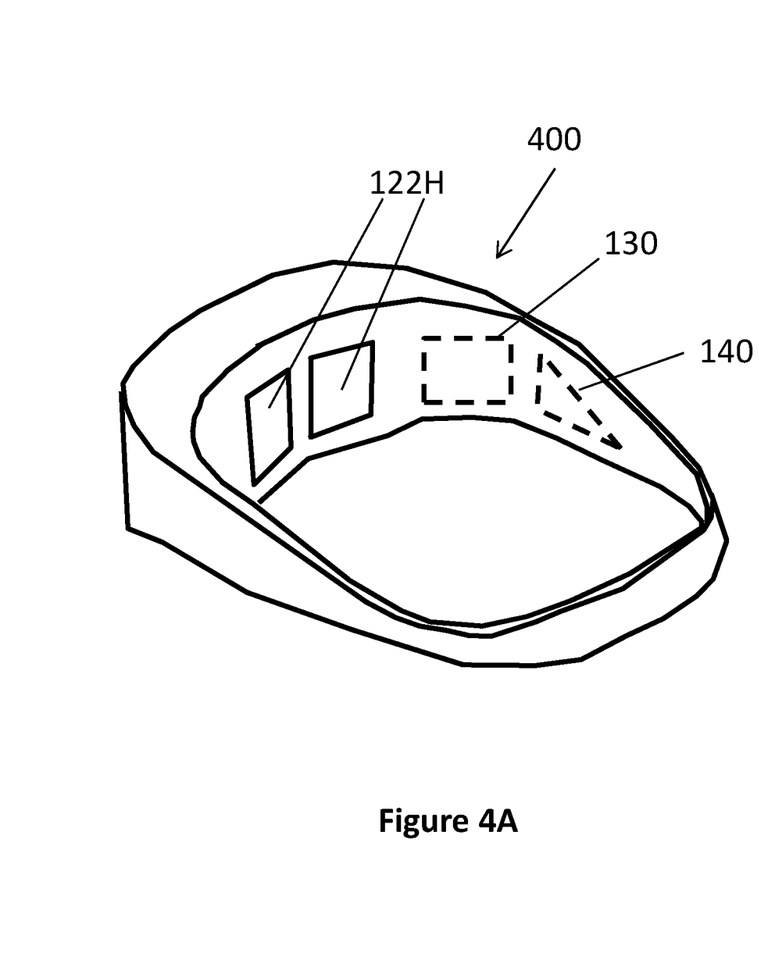
FIGS. 4A and 4B show an illustration of a magnification headset according to at least some embodiments of the present invention.
Figure 4B:
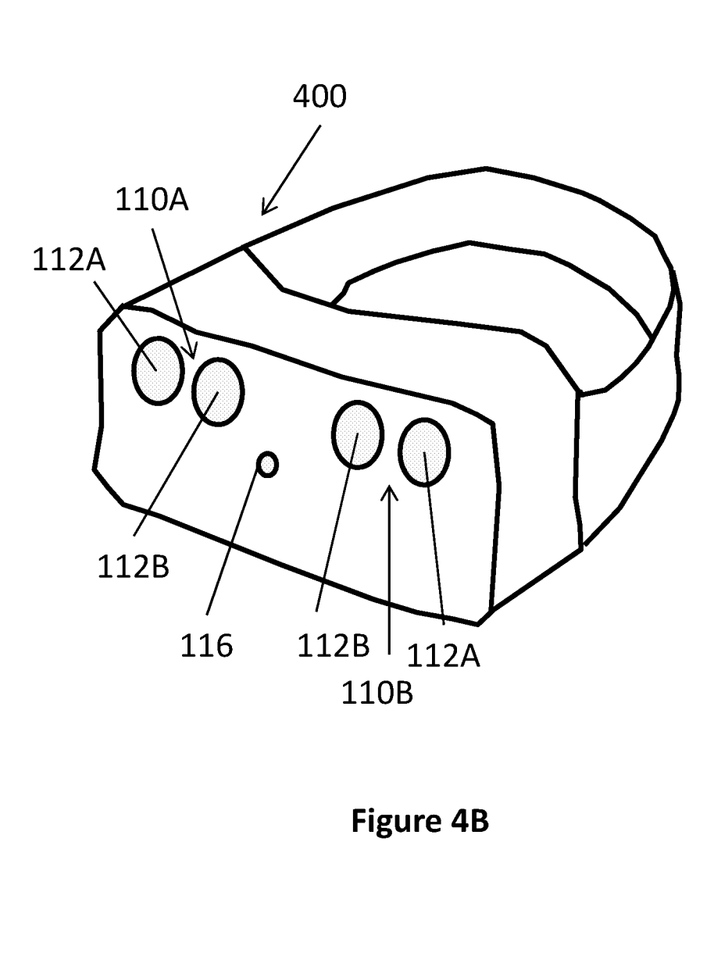

Reference is now made to FIGS. 4A and 4B which show an illustration of a magnification headset according to at least some embodiments of the present invention. Magnification headset 400 is a headset as known in the art providing the functionality of glasses 100 in a headset arrangement. Items with the same drawing numbers as used above with reference to FIGS. 1A-1E have the same functionality. Magnification headset 400 may also be referred to herein as a "wearable display" or as "magnification glasses".

Headset 400 comprises camera assemblies 110 each comprising two cameras 112A and 112B. The images from camera assemblies 110 are displayed on viewers 122H where each of viewers 122H are screens mounted in headset 400 and positioned in front of the eyes of the wearer of headset 400. Optionally a single screen 122H is provided that is divided into two viewing portions (left and right) Optionally camera assemblies 110 comprise more than two cameras each.

Camera assembly 110 is connected to a processor 130 and a power source 140 that are embedded inside headset 400. The electrical connections between camera assembly 110 and the processor 130 and power source 140 are made using cables embedded inside headset 400. The image sensor 162 of each camera 112 communicates with the processor 130 using any suitable protocol such as the non-liming example of the MIPI Camera Serial Interface.

Optionally headset 400 is connected to an external camera 132 by either wired or wireless connection. The image captured by external camera 132 is provided to the processor 130 for transmitting to viewer assembly 120.

The type of video or image shown on screens 122H may be any one of the following:

Magnification: where the view is the magnified video or image captured by camera assembly 110;

Virtual reality (VR): where the projected VR view is constructed by processor 130 or alternatively by a connected external processor (not shown);

Augmented reality (AR): Where the view captured by camera assembly 110 is augmented with data or other indications where the AR view is constructed by processor 130 or alternatively by a connected external processor (not shown);

Data view: where data related to the particular application is displayed to the user as described above with reference to FIGS. 3E and 3F;

Infrared view: where the view is the IR video or image captured by camera assembly 110 when camera assembly 110 comprises at least one IR camera;

External camera view: where the view is the view captured by an external camera 132 connected to headset 400.

Figure 5:
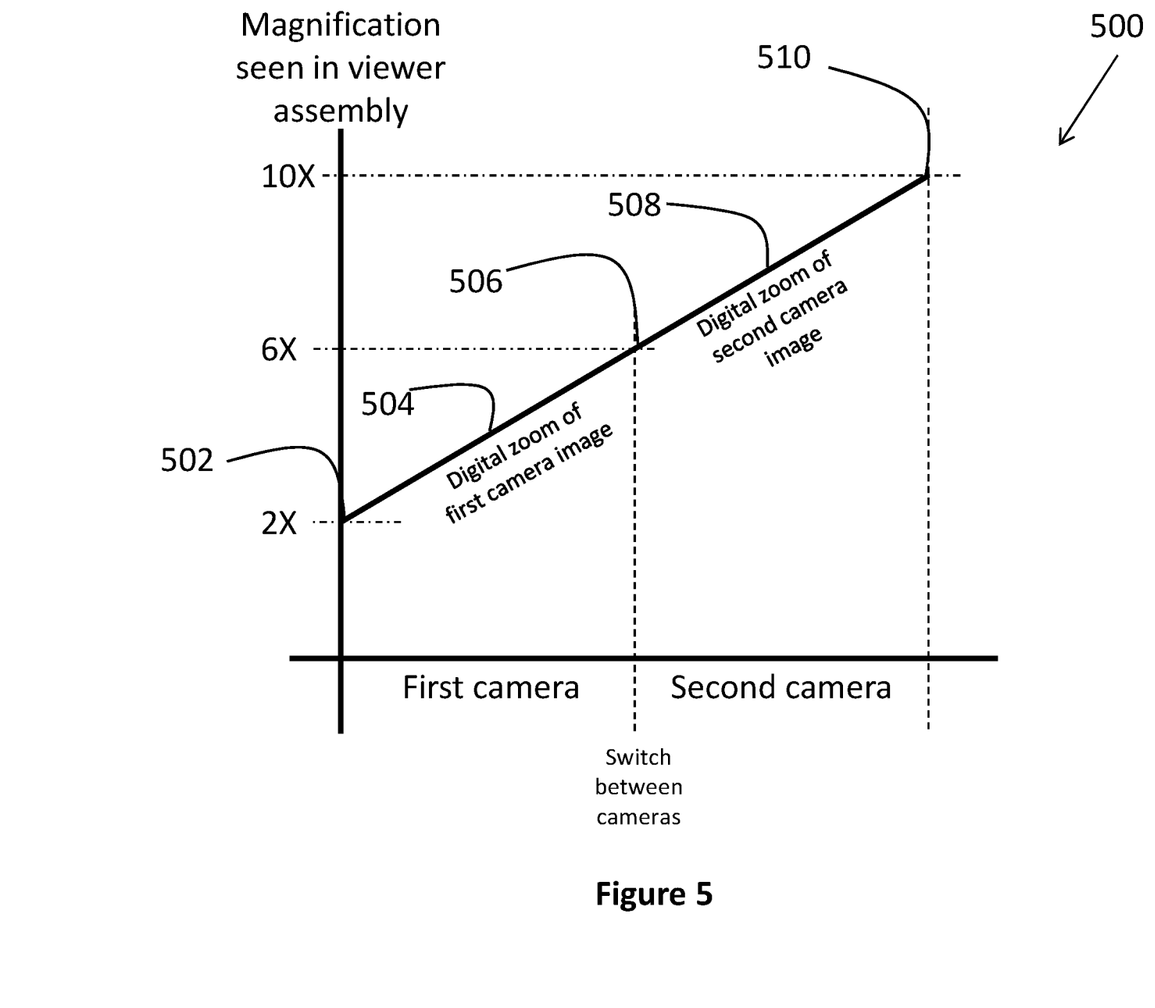
FIG. 5 shows an illustrative graph of the level of magnification provided by a magnification glasses according to at least some embodiments of the present invention.

Reference is now made to FIG. 5 which shows an illustrative graph of the level of magnification provided by a magnification glasses according to at least some embodiments of the present invention. The graph 500 shows magnification for glasses 100, 200 or 400 as described in hereinabove. For graph 500 camera assembly 110 comprises two cameras 112A and 112B, wherein first camera 112A provides magnification of 2× and second camera 112B provides magnification of 6×. These magnification levels are illustrative and should not be considered limiting.

As shown in graph 500, the magnification of the captured image shown on viewing assembly 120 varies between 2× and 10×. The working distance remains fixed at a specific working distance even as the magnification changes. At point 502, controller 130 transmits the output of first camera 112A to viewing assembly 120 such that the captured image is shown with a magnification of 2×. On slope 504 of graph 500 the image of camera 112A is digitally zoomed by controller 130 such that the captured image is shown with increasing magnification. The increase in magnification is preferably triggered by a user of the glasses activating controller buttons 124 such as a button (not shown) for increasing magnification.

At point 506 of graph 500, the image of camera 112A is digitally zoomed by controller 130 such that the captured image is shown on the viewing assembly with 6× magnification. At this point controller transmits the output of second camera 112B to viewing assembly 120 such that the captured image is shown with a magnification of 6×. The switch at point 506 between the capture of first camera 112A and the capture of second camera 112B is preferably seamless and the user of glasses is not aware of the switch. On slope 508 of graph 500 the image of camera 112B is digitally zoomed by controller 130 such that the captured image is shown with increasing magnification. As before the increase in magnification is preferably triggered by a user of the glasses activating controller buttons 124 such as a button (not shown) for increasing magnification.

It should be appreciated that the magnification of the captured image displayed on viewing assembly 120 is therefore in the range of 2×-10× and may be increased or decreased between this range by the user activating controller buttons 124. When the output magnification decrease below 6× at point 506, controller 130 switches from camera 112B to camera 112A.

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein. Combinations of the above embodiments are also considered. As a non-limiting example, the headset of FIGS. 4A and 4B could use the projectors as described for the viewing assembly of FIGS. 1A-1E.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. Magnification glasses comprising: a first camera array for capturing a magnified image in the field of view of said glasses comprising at least a first camera and a second camera wherein each of said first camera and said second camera provide different levels of magnification, wherein said first camera and said second camera have the same working distance, wherein said first camera and said second camera are fixed focus cameras.

2. The glasses of claim 1 wherein said working distance is between 150 mm to 400 mm.

3. The glasses of claim 2 wherein each of said first and second cameras provides a different magnification of between 2× and 10×.

4. The glasses of claim 3 further comprising a first viewer assembly and a processor, wherein said processor receives a first magnified image captured by said first camera and a second magnified image captured by said second camera and transmits either one of said first image or said second image for display on said first viewer assembly, wherein said processor is a computing device.

5. The glasses of claim 4 wherein said processor digitally zooms either one of said first magnified image or said second magnified image before transmission to said first viewer assembly.

6. The glasses of claim 5 wherein said first viewer assembly comprises at least one of:

a. a display screen positioned in front of said glasses frame;
   b. a display screen mounted in said glasses frame; or
   c. a projector for projecting on a lens in said frame.

7. The glasses of claim 6 wherein one or more of said cameras comprises an infrared camera.

8. The glasses of claim 7 wherein said processor provides for display on said viewer assembly at least one of:

a. said magnified view captured by said camera assembly;
   b. a virtual reality view;
   c. an augmented reality view;
   d. a data view; or
   e. an infrared view.

9. The glasses of claim 8 further comprising a second camera array and a second viewer assembly positioned on the same side of said glasses, wherein said first camera array and a first viewer assembly are positioned on the opposite side of said glasses wherein said first and second camera arrays are spaced horizontally apart so as to capture stereoscopic vision, wherein the said processor transmits the image from said first camera array to said first viewer assembly and wherein said processor transmits the image from said second camera array to said second viewer assembly.

10. The glasses of claim 9 further comprising an illumination source.

11. The glasses of claim 10 wherein said illumination source comprises an ultraviolet light.

12. The glasses of claim 5 wherein said processor switches between said first magnified image and said second magnified image at a point where said first magnified image and said second magnified image appear the same to a user of said glasses.

13. Electro-optical magnifying glasses comprising:

a. a wearable display; and
   b. a first camera array for capturing a magnified image in the field of view of said glasses comprising at least a first camera and a second camera wherein each of said first camera and said second camera provide different levels of magnification, wherein said first camera and said second camera have the same working distance, wherein said first camera and said second camera are fixed focus cameras.

14. The glasses of claim 13 wherein said working distance is between 150 mm to 400 mm.

15. The glasses of claim 14 wherein each of said first and second cameras provides a different magnification of between 2× and 10×.

16. The glasses of claim 15 further comprising a processor, wherein said processor receives a first magnified image captured by said first camera and a second magnified image captured by said second camera and transmits either one of said first image or said second image for display on said display, wherein said processor is a computing device.

17. The glasses of claim 16 wherein said processor digitally zooms either one of said first magnified image or said second magnified image before transmission to said first viewer assembly.

18. The glasses of claim 17 wherein one or more of said cameras comprises an infrared camera.

19. The glasses of claim 18 wherein said processor provides for display on said display of at least one of:

a. said magnified view captured by said camera assembly;
   b. a virtual reality view;
   c. an augmented reality view;
   d. a data view; or
   e. an infrared view.

20. The glasses of claim 16 wherein said processor switches between said first magnified image and said second magnified image at a point where said first magnified image and said second magnified image appear the same to a user of said glasses.

* * * * *